United States Patent [19]

Rosenstein

[11] 4,054,220
[45] Oct. 18, 1977

[54] COMBINED POCKET FLASK AND DENTURE CASE WITH REMOVABLE CUP PORTION

[76] Inventor: Abraham J. Rosenstein, R.R. No. 1, Canaan, Conn. 06018

[21] Appl. No.: 659,477

[22] Filed: Feb. 19, 1976

Related U.S. Application Data

[63] Continuation-in-part of Ser. No. 609,968, Sept. 3, 1975, abandoned.

[51] Int. Cl.$^2$ .......................... B08B 3/04; B65D 1/04; B65D 81/08
[52] U.S. Cl. ........................................ 215/6; 134/117; 206/523; 215/1 C
[58] Field of Search .................... 134/117, 137; 21/84; 206/38, 83, 210; 215/6

[56] References Cited

U.S. PATENT DOCUMENTS

| | | | |
|---|---|---|---|
| 193,025 | 7/1877 | Newton | 215/6 X |
| 1,064,442 | 6/1913 | Cadigan | 215/6 |
| 2,611,499 | 9/1952 | Mayer | 215/6 |
| 3,469,739 | 9/1969 | Phillips | 215/6 |
| 3,732,999 | 5/1973 | Rounkles | 215/6 |
| 3,802,919 | 4/1974 | Saffir | 206/38 |
| 3,880,278 | 4/1975 | Brown | 134/137 |
| D. 55,068 | 5/1920 | McDonnel et al. | D9/46 |
| D. 219,366 | 12/1970 | Lewis et al. | D9/46 |

*Primary Examiner*—Daniel Blum
*Attorney, Agent, or Firm*—Miller & Prestia

[57] ABSTRACT

A compact, portable pocket flask for cleaning and refreshing dentures. The flask is elongated, elliptically-shaped and pocket sized and contains two completely sealed compartments also sealed from each other. One such compartment is shaped to carry a denture for cleaning purposes, and is accessible through inverting of the flask and removing the cup portion which seals the fluid in the lower compartment. This lower flask compartment has padded walls, and is completely sealed by means of said cup portion, whereby the denture within the compartment may be treated by shaking the flask. The other compartment is connected to the neck of the flask and may contain rinsing fluid such as mouthwash or water; or by means of the sealing "cup" enables transfer of fluid from the upper compartment to the lower compartment.

4 Claims, 4 Drawing Figures

COMBINED POCKET FLASK AND DENTURE CASE WITH REMOVABLE CUP PORTION

BACKGROUND OF THE INVENTION

This is a continuation-in-part of my application Ser. No. 609,968, filed Sept. 3, 1975 and now expressly abandoned, which in turn was a an improvement of my application Ser. No. 499,571, issued as U.S. Pat. No. 3,904,058 on Sept. 9, 1975.

This invention relates to a compact, portable pocket flask which fits easily into a pocket or purse, and which may be used privately for denture cleaning and mouth rinsing purposes. Its portable nature, and the ease of its use, adapt it for service at almost any time or place, such as in the private stalls in washrooms, for example, while the removal and cleaning of a denture might otherwise be a source of embarrassment to its owner. Moreover, the attractive design of the flsk and accessories provide an aesthetically pleasing, yet functionally effective denture cleaning device

DISCUSSION OF THE PRIOR ART

The patent to Crawford U.S. Pat. No. 3,732,973 discloses a combined denture case and brush, which is a large cup of such a size and shape as to preclude its use as a portable carrier easily placed into and removed from its owner's pocket, purse or the like. Many other devices of the type of the Crawford patent have been disclosed in the patent literature, including the denture bath shown in the patent to Leifman et al U.S. Pat. No. 3,386,706 and various vibratory devices for cleaning dentures, such as that shown in the patent to George U.S. Pat. No. 3,151,846.

One of the problems in the prior art is that there is no aesthetically pleasing completely portable, small, compact carrying device which can readily be carried in the pocket or purse of a person who is traveling or who, for any other reason, does not have the full and exclusive use of washroom facilities.

OBJECTS OF THE INVENTION

It is accordingly an object of this invention to provide an aesthetically appealing, compact, portable carrier which can be used with convenience and privacy for denture cleaning, even while traveling or otherwise obliged to use public toilet facilities, all without embarrassment to the user. Still a further object of this invention is to provide a portable pocket flask which can be carried in the pocket of the user and which can be used with efficiency and effectiveness in brushing and cleaning of dentures in any location without depending upon the availability of running water such as in the privacy of a toilet stall in a large public washroom area.

Other objects and advantages of this invention, including the simplicity, economy and effectiveness thereof, and the gentleness with which it stores and processes the dentures, will further become apparent hereinafter and in the drawings.

DRAWINGS

Figure 1:
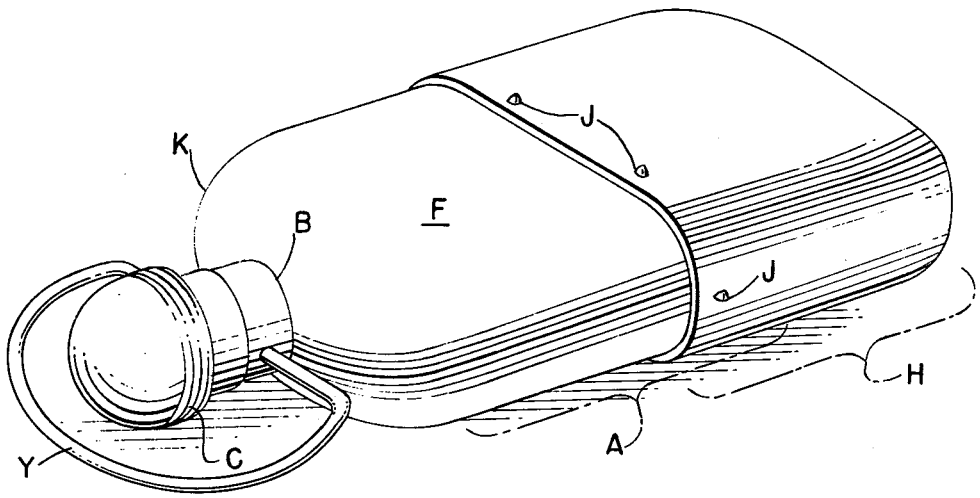
FIG. 1 is a view in perspective showing one form of flask and cup embodying features of the invention.

Referring to the drawings, the letter A designates the flask, having a neck B at one end, sealingly closed at a knobbed screw cap C. Ring-shaped holding member Y is pivotally attached to neck B to facilitate easy grasping of the flask.

Figure 2:
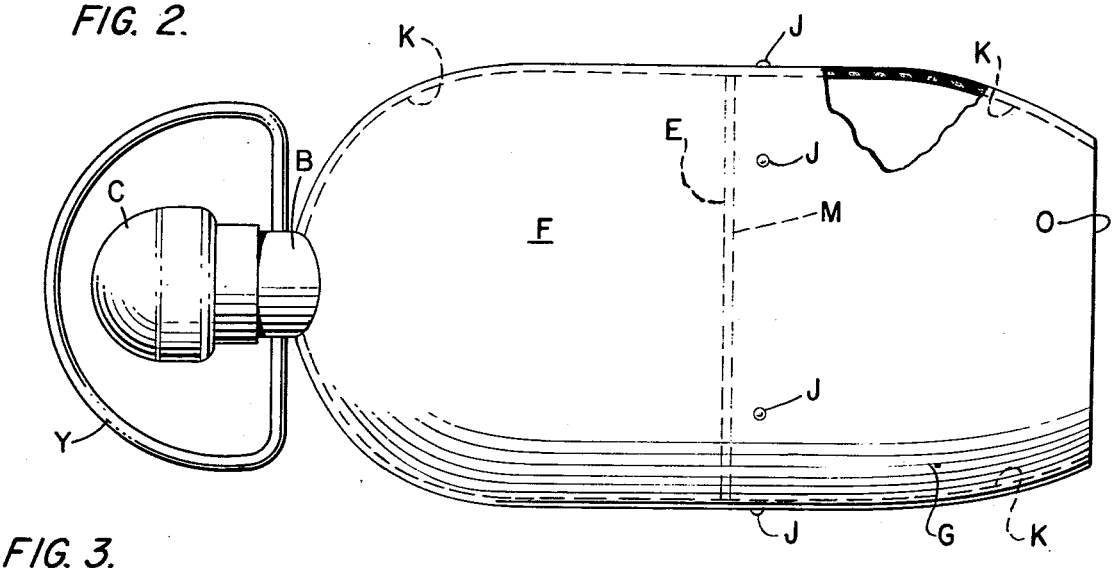
FIG. 2 is a side view of a flask shown in FIG. 1, with open lower (denture) compartment showing the flask without the cup portion that also seals the lower compartment.

As shown in FIG. 2 the flask A has boundary walls K and an open end O which define the container. Through open end O fluid is introduced into the lower compartment while open end O allows for insertion of dentures while the flask is held in inverted position. There is also a transverse wall E which sealingly divides the internal portion of the container into a compartment F which communicates with the neck portion B and another compartment G which is spaced from the compartment F. As shown in FIG. 2 the compartment G is smaller than the compartment F although this relationship may vary.

The compartment G is completely open at the bottom of the flask, here shown as having no bottom; and is covered by a rectangular or elliptical cup H (shown in FIG. 3) shaped so as to seal compartment G or act as a transfer cup for transferring liquid from compartment F to compartment G. Fasteners J consist of male and female clips that lock together to secure and to release cup H with respect to the flask and compartment G.

Figure 3:
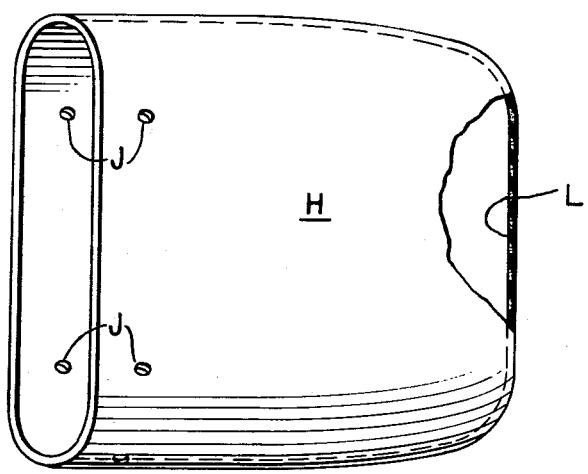
FIG. 3 is a view in perspective showing the cup portion used also for sealing the lower compartment.
Figure 4:
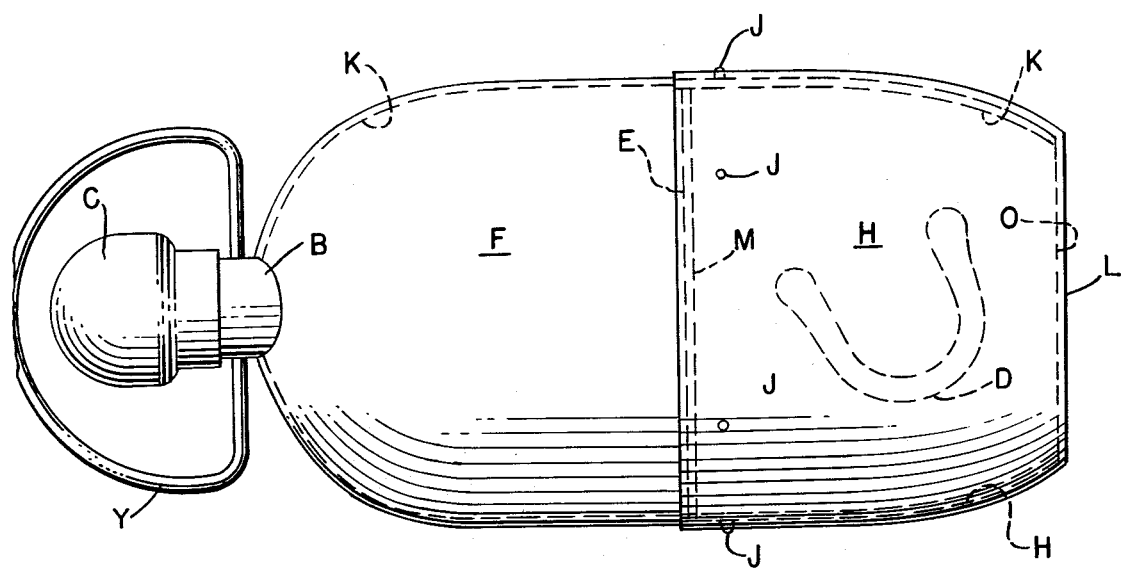
FIG. 4 is a side view of a flask shown in FIG. 1 with inserted denture for cleaning and sealed with the cup portion.

Referring to FIG. 3, a separatable cup H is provided to seal compartment G of the flask, or use for transferring fluid from compartment F to compartment G or from other fluid sources. Said cup H fits snugly and snaps onto the lower portion of the flask by means of snaps J forming a sealing relationship with compartment G. Further, the inner side walls K and bottom wall L of cup H as well as the inner wall M of the panel wall E are lined with soft resilient material such as foam rubber or the like, thus forming a protective and cushioning enclosure for denture D.

Operation

In operation, it will be apparent that the compartment F may be used to store water, mouthwash liquid or any other liquid of user's choosing. Similarly, a denture cleansing liquid may be contained within the compartment G which is normally kept in a sealed and closed condition while it is carried in the user's pocket, purse, briefcase, or the like. At any appropriate time during the day or night, when the user desires to cleanse the dentures D, he simply locates a reasonably private area such as a stall within the public toilet facilities for example, and uses the compartment G to cleanse the denture D. This is readily accomplished by simply inverting the flask A and removing cup H thereby opening compartment G while holding the flask inverted with opening O facing upwardly, then inserting the denture D into the cleanser fluid already contained therein, snapping on cup H into sealing contact with the flask body, securing it in sealed position by causing snaps or equivalent locking device to fall in place, and then shaking the entire flask together with its contents for the desired period of time. The denture D is protected against breakage or damage because of the softness and resilience of the walls K, L, and M, and after an appropriate time the compartment G may be opened up and the denture D removed and the remaining liquid emptied into the toilet bowl. At this stage, the compartment G may be sealed shut again by reapplying cup H; or, if desired the user may avail himself of the use of a new mouthwash or ordinary tap water from a basin in the public area or from compartment F by simply using cup H as a transfer cup, thus readying compartment G for quick use again whenever next necessary. After use the compartments F and G are sealed, the flask replaced in the user's pocket, purse, briefcase, or the like, and the task of cleaning the denture D has been quickly, conveniently and reasonably privately performed.

It is important, as will be apparent, that the compartment flask must be water-tight, that it must be of such shape and form as to enable easy carrying in one's pocket or in a woman's purse, for example, and the provision of the inner wall lining such as foam rubber or the like is highly important in preventing injury or damage to the denture D.

The upper compartment F may be of a much smaller size than shown in the drawing. Further, the overall sizes and the relative sizes of the two compartments may be varied at will, subject to the size which is desired, and which will enables the entire flask to be placed in one's pocket or purse, for example.

It is to be emphasized that the purpose of the container in accordance with this invention is not storage, but it is intended only for use as a quick cleansing means in screened-off private portions of public areas while at the same time avoiding any possibility of embarrassment in use.

While it is not essential, it is desired to provide a somewhat elliptical shape for the combined compartments, to enable easy pocketing or purse storing. In this connection, it is highly preferred that the flask be long, flat and thin, and somewhat compact, like a wallet.

Obviously, the seals are very carefully constructed, because leakage would be disastrous.

Although this invention has been described with reference to a certain specific form thereof, it will be appreciated that many variations may be made without departing from the spirit and scope of the invention as defined in the appended claims.

The following is claimed:

1. A compact, portable pocket flask denture storage and cleaning apparatus comprising an elongated, pocket size flask of a size and shape for ready insertion into and removal from a standard size pocket or handbag, said flask an integral having transverse dividing wall internally separating the space within said flask into aligned upper and lower compartments each of which is sealed from the other, said flask having a neck portion connected to said upper compartment, said neck portion being provided with a water-tight cap for sealing liquid therein, the lower compartment of said flask being completely open at the bottom, which bottom is spaced apart from said transverse dividing wall to provide a lower space within said flask, which lower space is sealed from said upper space, and means in the form of a cup which is shaped to fit snugly over the outside surfaces of said lower compartment in a manner to form a seal therewith, said cup having an open top and having a closed and sealed bottom, said cup having an inner bottom wall lined with soft and resilient material and said cup being of a size sufficient to contain a denture, and the inside walls of said lower compartment also lined with soft and resilient material, thus forming a protective and cushioning enclosure for the denture.

2. The pocket flask defined in claim 1, wherein said cup and said lower portion of said flask have mating clasp members by which they may be secured to one another.

3. The pocket flask defined in claim 1, wherein the upper and lower compartments have a substantially elliptical cross-section.

4. The pocket flask defined in claim 1, further to include a ring-shaped holder member pivotally mounted to said neck.

* * * * *